(12) United States Patent
Tsuda et al.

(10) Patent No.: US 6,706,177 B2
(45) Date of Patent: Mar. 16, 2004

(54) OPEN CAPILLARY COLUMN AND MANUFACTURING METHOD THEREOF

(75) Inventors: Takao Tsuda, 3102, Kaguyama 2-chome, Nisshin-shi, Aichi (JP); Shinya Kitagawa, Nagoya (JP); Motonori Munesue, 178-11, Kitashinmachi 6-chome, Matsubara-shi, Osaka (JP)

(73) Assignees: Takao Tsuda, Aichi (JP); Chemco Scientific Co. Ltd., Osaka (JP); Motonori Munesue, Osaka (JP)

( * ) Notice: Subject to any disclaimer, the term of this patent is extended or adjusted under 35 U.S.C. 154(b) by 19 days.

(21) Appl. No.: 10/119,132

(22) Filed: Apr. 8, 2002

(65) Prior Publication Data

US 2003/0189001 A1 Oct. 9, 2003

(51) Int. Cl.[7] .................................. B01D 15/08
(52) U.S. Cl. ................. 210/198.2; 210/502.1; 210/635; 210/656; 95/88; 96/101
(58) Field of Search ................ 95/88; 96/101; 210/635, 656, 658, 198.2, 198.3, 502.1

(56) References Cited

U.S. PATENT DOCUMENTS

| | | | | |
|---|---|---|---|---|
| 4,054,432 A | * | 10/1977 | Taylor et al. | 96/101 |
| 4,131,542 A | * | 12/1978 | Bergna et al. | 210/656 |
| 4,169,790 A | * | 10/1979 | Pretorius et al. | 210/656 |
| 4,207,188 A | * | 6/1980 | Tsuda et al. | 210/198.2 |
| 4,276,061 A | * | 6/1981 | Nestrick et al. | 95/88 |
| 4,293,415 A | * | 10/1981 | Bente et al. | 210/198.2 |
| 5,082,559 A | * | 1/1992 | Eguchi et al. | 210/198.2 |
| 5,620,603 A | * | 4/1997 | Betz et al. | 210/635 |
| 5,637,135 A | * | 6/1997 | Ottenstein et al. | 96/101 |
| 6,251,280 B1 | * | 6/2001 | Dai et al. | 210/656 |
| 6,616,825 B1 | * | 9/2003 | Frechet et al. | 204/605 |

* cited by examiner

Primary Examiner—Ernest G. Therkorn
(74) Attorney, Agent, or Firm—Akin Gump Strauss Hauer & Feld LLP

(57) ABSTRACT

In an open capillary column, a stationary phase is formed on the inner wall of a capillary tube. This stationary phase comprises a number of pores on the surface of the capillary tube, and each of pore has an expanded hollow in the stationary phase. A manufacturing method of an open capillary column comprises the steps of giving alkaline treatment to an inner wall of an open capillary tube, applying one of oligo silica, oligo zirconia and oligo titania on the inner wall, filling the open capillary tube with alkaline solution to form one of a silica layer, a zirconia layer and titania layer, discharging the alkaline solution and heat-treating the capillary tube to form a base of a stationary phase. The open capillary column of the present invention comprises a stationary phase having a very large surface area. It is useful for a separation analysis field such as liquid chromatography and electrochromatography.

12 Claims, 5 Drawing Sheets

OPEN CAPILLARY COLUMN AND MANUFACTURING METHOD THEREOF

BACKGROUND OF THE INVENTION AND DESCRIPTION OF RELATED ART

The present invention relates to an open capillary column which may be provided for a separation analysis field such as liquid chromatography and electrochromatography, and manufacturing method thereof.

In a conventional open capillary column, it is rare that an excellent chromatogram is obtained under a reversed-phase condition of a chemical-modification type open capillary column in liquid chromatography and, simultaneously, the relative retention value is equal to or larger than 0.5 under condition of a 50% methanol solution. The relative retention is determined by the size of the surface area of a stationary phase and the thickness of the phase. However, since the thickness of the stationary phase relates to a mass transfer coefficient, if the stationary phase is too thick, a chromatogram displaying excellent separation is not obtained. Consequently, development of a stationary phase having a large surface area is not so advanced.

As columns for electrochromatography, there are three columns of a packed-type capillary column, a loosely packed column, and an open capillary column. In the electrochromatography, a voltage is applied in the column axis direction. Consequently, a current flows in the column and Joule's heat is generated. Bubbles may be generated in the column due to the Joule's heat. In the case where bubbles are generated, the operation has to be stopped once to remove the bubbles from the column. To solve the problem of bubbles, another problem arises from the viewpoint of operation such that the column has to be washed with high voltage of the liquid chromatography. Ease of the removing operation is the key to obtain a stable operation of electrochromatography. Therefore, it is the most effective to employ an open capillary column as a column for electrochromatography.

Conventionally, as a material of a glass capillary tube, soda glass is used. A chemical treatment on the surface of glass is easy, and an excellent silica stationary phase is realized by deposition of silica which occurs simultaneously with fusion of the glass surface by sodium hydroxide solution. However, soda glass is brittle and easily bent, so it is not suitable for wide use. At present, fused silica capillary glass is widely employed as very stable glass. However, the glass surface of the material is very stable, and it is very difficult to enlarge the surface area by chemical treatment. Although the surface of the fused silica capillary glass may be etched by a treatment at high temperature (for example, 350° C. to 400° C.) with an ammonium bifluoride reagent, an excellent column has not been achieved yet by the method. A surface treatment under severe conditions is accompanied by deterioration of a column in the long term.

There is a case that a column developed as a stationary phase extracting tube for gas chromatography is properly cut to be short and the resultant is used for collecting samples. Inherently, in the case of dealing with a sample of liquid or solution, a sample collection tube developed for liquid is desirable. When an open capillary tube is used as a sample collection tube, the flow resistance is low at the time of collecting samples and sampling operation may be easily performed. An open capillary tube, that is, a short capillary column in which a stationary phase of a large sample addition amount provided for this purpose is formed is desired. However, a material having proper functions of such an open capillary tube does not exist yet.

An object of the present invention is therefore to provide a column in which a stationary phase having a very large surface area is formed as an open capillary column provided for a separation analysis field such as liquid chromatography and electrochromatography and to provide a method of manufacturing the column.

SUMMARY OF THE INVENTION

In an open capillary column of the present invention, a stationary phase is formed on the inner wall of an open capillary tube. The stationary phase comprises a number of pores on the surface, and each of pore has an expanded hollow in the stationary phase.

In the present invention, the open capillary tube may be a fused silica capillary tube.

Further, the open capillary tube may be obtained by cutting an open capillary tube material with an arbitrary proper length.

In the present invention, as a base material of the stationary phase, oligo silica, oligo zirconia or oligo titania may be used.

Further, the stationary phase may be chemically modified stationary phase by adding chemically modification. Specifically, the surface of the stationary phase and/or the expanded hollows in the stationary phase may be subjected to chemical modification, thereby obtaining a chemically modified stationary phase. In this case, the surface of the stationary phase and the expanded hollows in the stationary phase may be subjected to different chemical modifications, thereby obtaining a chemically modified stationary phase.

In the present invention, as a functional group of chemical modification, any of alkyl group, γ-aminopropyl group, cyanoethyl group, cyclodextrin group, and ion exchange group may be selected.

In an open capillary column of the present invention, the inner wall of the open capillary tube is subjected to alkaline treatment. Subsequently, oligo silica, oligo zirconia, or oligo titania is applied on the inner wall, and the open capillary tube is filled with an alkaline solution to form a silica layer, a zirconia layer, or a titania layer. The alkaline solution is discharged and, after that, the capillary tube is subjected to heat treatment, thereby forming a base of a stationary phase.

The above and other objects and effects of the invention will become apparent in the following description with reference to the accompanying drawings.

DETAILED DESCRIPTION OF THE INVENTION

Figure 1:
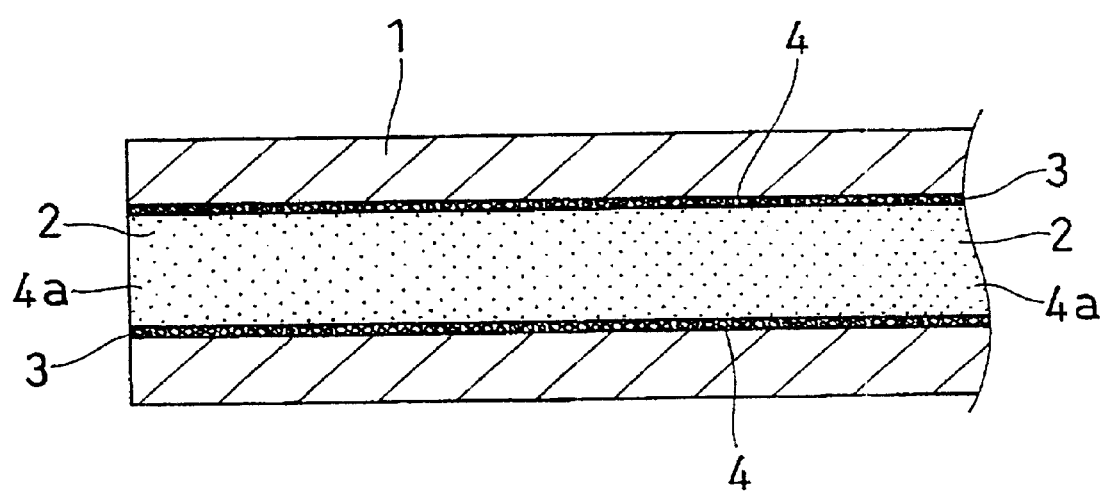
FIG. 1 is an enlarged cross section of an open capillary column of the present invention.
Figure 2:
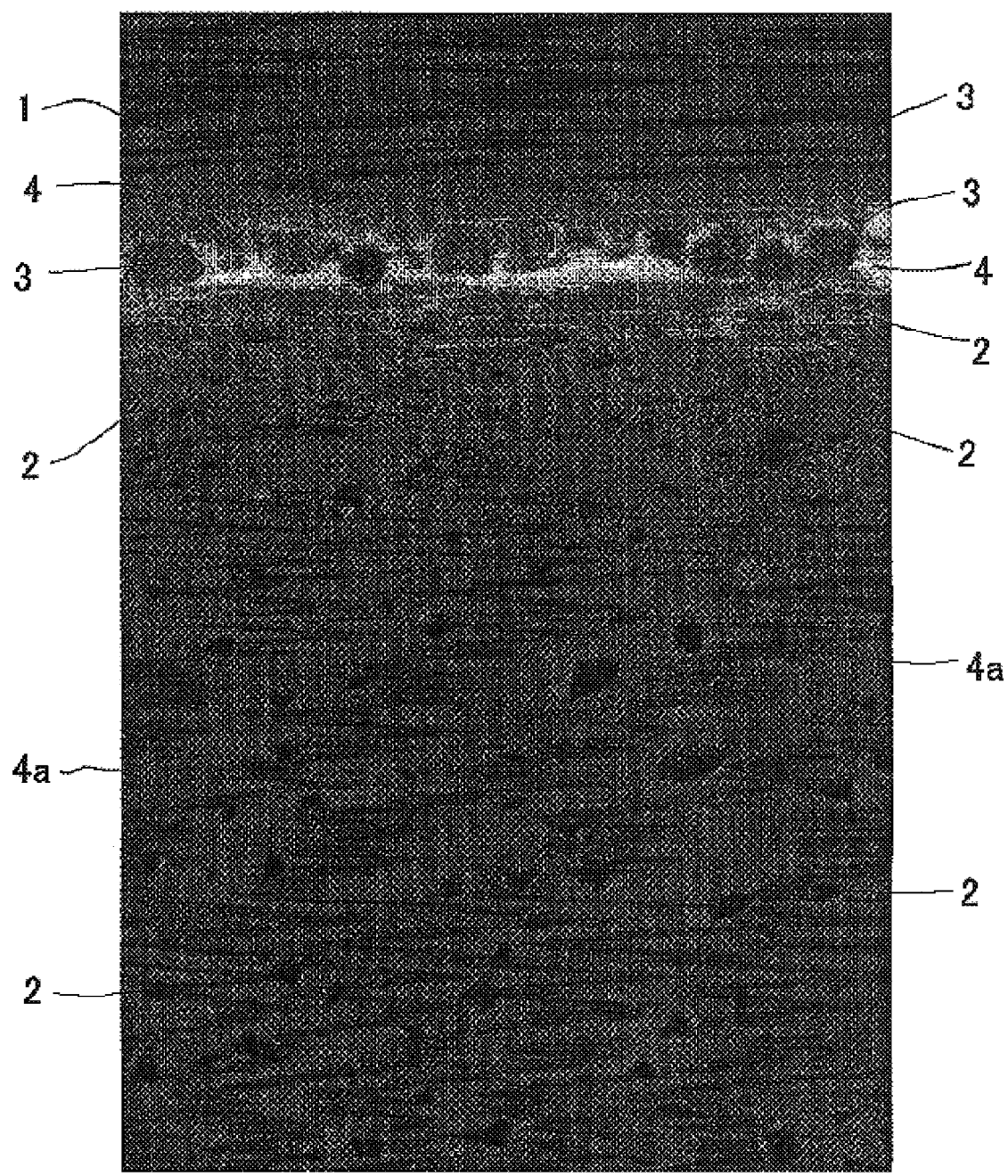
FIG. 2 is a microphotograph diagram captured by further enlarging a part of the open capillary column of the present invention.

FIG. 1 is an enlarged cross section of an open capillary column of the present invention. FIG. 2 is a diagram of microphotograph captured by further enlarging apart of the open capillary column of the present invention. As shown in FIGS. 1 and 2, on the inner wall of an open capillary tube 1, a stationary phase 4 is formed. It comprises a number of pores 2 on the surface 4a, and each of pore has an expanded hollow 3 in the stationary phase.

In the present invention, the open capillary tube 1 may be a fused silica capillary tube. In the open capillary tube 1, at the time of collecting samples, the flow resistance is low and the sample collecting operation is easy. Consequently, the open capillary tube 1 for chromatography in which a stationary phase of a large sample load amount is formed may be obtained by cutting an open capillary tube material with an arbitrary proper length, as a stationary phase extracting tube. It may be therefore used as a collecting tube having ability of efficiently collecting a diluent sample.

In the present invention, the expanded hollow 3 may be a hollow which is wider than the pore 2 on the surface 4a of the stationary phase 4. The thickness of the stationary phase 4 may be about 0.2 to 0.9 $\mu$m, the diameter of the pore 2 is about 0.1 to 0.5 $\mu$m, and the inside diameter of the hollow 3 is about 0.2 to 0.8 $\mu$m. However, the present invention is not limited to the numerical values.

In the present invention, a base material of the stationary phase 4 may be oligo silica, oligo zirconia or oligo titania. The stationary phase 4 may be subjected to chemical modification, thereby obtaining the chemically modified stationary phase. Specifically, the surface 4a of the stationary phase 4 and/or the expanded hollow 3 in the stationary phase 4 are/is subjected to chemical modification, thereby obtaining the chemically modified stationary phase. In this case, the surface 4a of the stationary phase 4 and the expanded hollow 3 in the stationary phase 4 may be subjected to different chemical modifications, thereby obtaining the chemically modified stationary phase. As the functional group of chemical modification, any of alkyl group, γ-aminopropyl group, cyanoethyl group, cyclodextrin group, and ion exchange group may be selected.

The open capillary column of the present invention is prepared by the following manufacturing process.

(Manufacturing Process 1: Process of Pre-Treatment)

As a pre-treatment, an alkaline treatment is performed on the inner wall of the open capillary tube at 80° C. for one hour so that oligo silica is easily fixed.

(Manufacturing Process 2: Process of Application of Oligo Silica)

Oligo silica is applied on the inner wall of the open capillary tube. Oligo silica used is a chemical substance obtained by polymerizing tetraethoxysilane and adjusting the polymerization degree to 10 to 20. Oligo silica has a structure very similar to that of quartz as a material of a capillary tube. Oligo silica is very easily adhered to the inner wall of the capillary tube and stability by fixation to the inner wall face promptly progresses. By using oligo silica having the polymerization degree of 10 to 20, the core for forming a silica layer is easily formed, and a thin film may be formed more stably by using oligo silica.

Oligo silica is applied by filling a fused silica capillary glass tube with an oligo silica solution, applying a gas pressure to one end of the capillary tube, and discharging the oligo silica solution from the tube. In the process, the oligo silica reagent remains in the capillary tube.

(Manufacturing Process 3: Formation of Silica Layer with Alkaline Solution)

The open capillary tube is filled with an ammonia solution and this state is maintained for one hour. During the period, formation of a silica layer is advanced. After that, the ammonia solution is discharged from the capillary tube.

(Manufacturing Process 4: Process of Heat Treatment)

While passing nitrogen gas into the capillary tube, heat treatment by continuously increasing temperature is given.

By the manufacturing processes, a stationary phase is formed on the inner wall of the open capillary tube. The stationary phase comprises a number of pores on its surface, and each of pore has an expanded hollow in the stationary phase. Although the thickness of the stationary phase varies according to the manufacturing process, as an example, a stationary phase having a thickness of 0.8 $\mu$m, the size of the pore of 0.3 $\mu$m, and the inside diameter of the expanded hollow of about 0.6 $\mu$m was formed. Since the thickness and the size of the pore depend on the concentration of ammonia, in another example in which the concentration of ammonia was different from that in the above example, a stationary phase having a thickness of 0.3 $\mu$m, the size of the pore of 0.15 $\mu$m, and the inside diameter of the expanded hollow of about 0.2 $\mu$m was formed.

To prepare the open capillary column of the present invention, in the manufacturing process 2, in place of oligo silica, oligo zirconia or oligo titania may be used.

Further, subsequent to the above manufacturing process, a manufacturing process of chemically modifying a stationary phase to obtain a chemically modified stationary phase may be also added. In the manufacturing process, the surface of the stationary phase and/or the expanded hollow in the stationary phase may be subjected to chemical modification, thereby obtaining a chemically modified stationary phase. In this case, the surface of the stationary phase and the expanded hollow in the stationary phase may be subjected to different chemical modifications, thereby obtaining a chemically modified stationary phase. As the functional group of chemical modification, any of alkyl group, γ-aminopropyl group, cyanoethyl group, cyclodextrin group, and ion exchange group may be selected.

By using an open capillary column with a chemically modified stationary phase formed by chemically modifying the stationary phase of the open capillary column manufactured by the above manufacturing processes, liquid chromatography and electrochromatography was carried out. As a result, as described below, an open capillary column having a long relative retention which has not been realized was provided.

Figure 3:
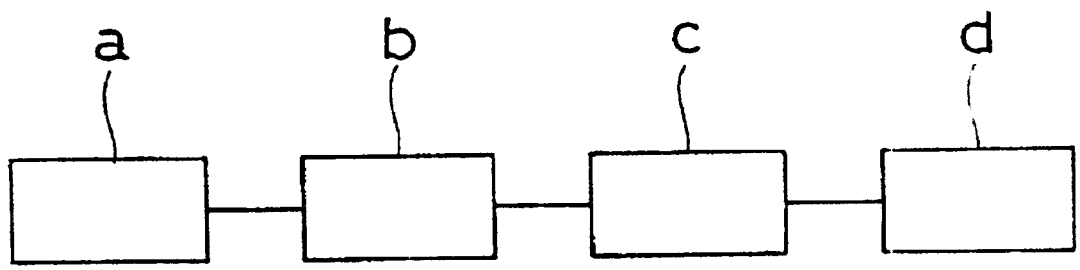
FIG. 3 is a block diagram of liquid chromatography using the open capillary column of the present invention.
Figure 4:
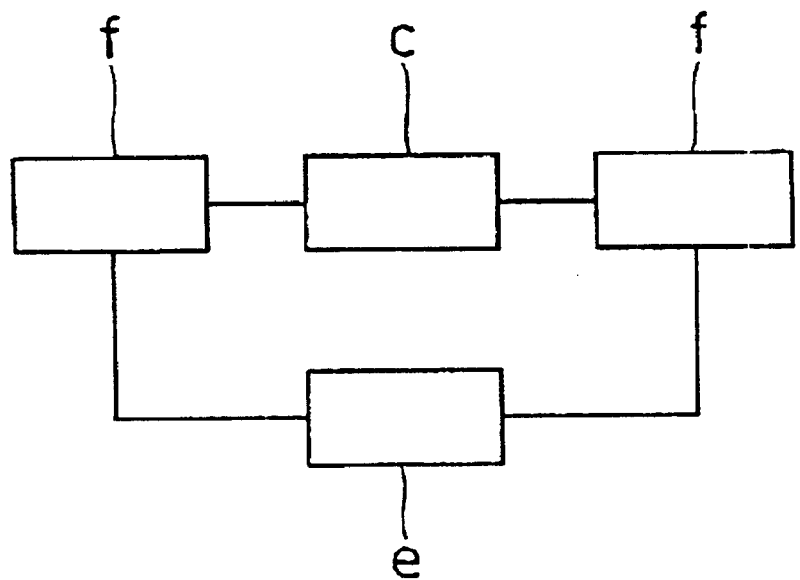
FIG. 4 is a block diagram of electrochromatography using the open capillary column of the present invention.

FIG. 3 is a block diagram showing a state where liquid chromatography is carried out by using the open capillary column of the present invention. "a" denotes a pump, "b" denotes a micro sample syringe, "c" indicates an open capillary column, and "d" expresses a detector. FIG. 4 is a block diagram showing a state where electrochromatography is carried out by using the open capillary column of the invention. "c" indicates an open capillary column, "e" indicates a high voltage power supply, and "f" denotes a solvent vessel.

Figure 5:
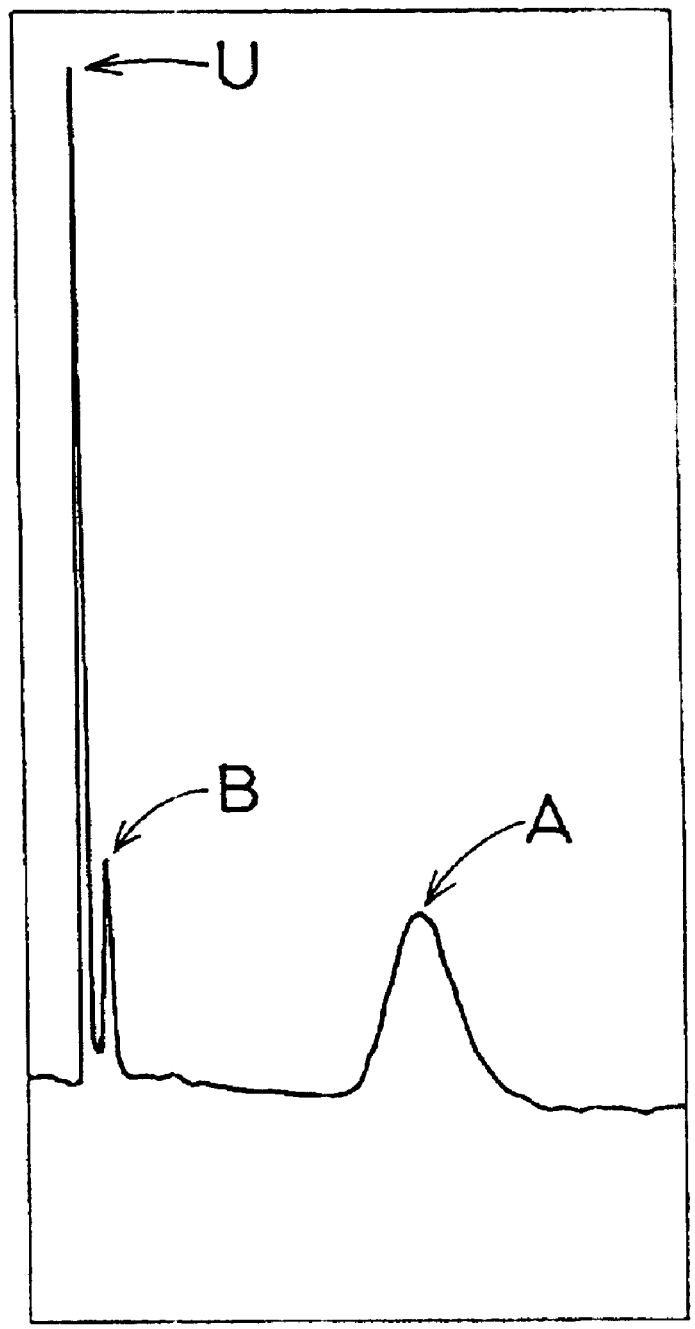
FIG. 5 shows a chromatogram obtained by the liquid chromatography using the open capillary column of the present invention.

In the liquid chromatography, a 45% methanol solution was used for a mobile phase and, as samples, uracil, benzene, and acenaphthene were used. As a column, an open capillary column having an inside diameter of 25 $\mu$m and a length of 40 cm, with a stationary phase obtained by chemically modifying octadecyl silane was used. U, B, and A in a chromatogram shown in FIG. 5 denote the peaks of uracil, benzene, and acenaphthene, respectively.

Figure 6:
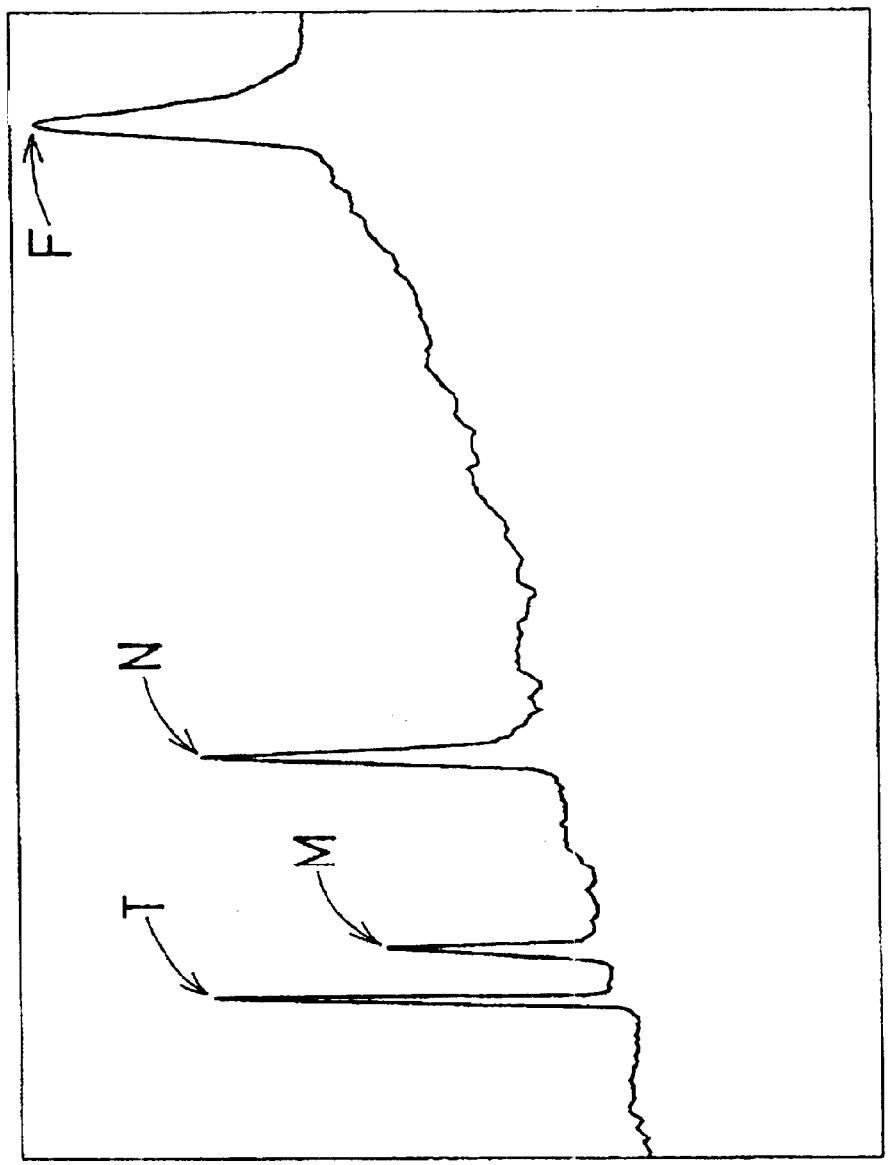
FIG. 6 shows a chromatogram obtained by the electrochromatography using the open capillary column of the present invention.

In the electrochromatography, a 1:1 mixture of methanol: 5 mM phosphate buffer (pH 7) was used for a mobile phase and, as samples, thiourea, methyl benzoate, naphthalene, and fluorene were used. As a column, an open capillary column having an inside diameter of 25 $\mu$m and a length of 45 cm, with a stationary phase obtained by chemically modifying octadecyl silane was used. T, M, N and F in a chromatogram shown in FIG. 6 denote the peaks of thiourea, methyl benzoate, naphthalene, and fluorene, respectively.

According to the present invention, with the configuration as described above, a column in which a stationary phase having a very large surface area is formed may be provided as an open capillary column for use in a separation analysis field such as liquid chromatography and electrochromatography. By using the column, separation displaying an excellent high separative ability may be realized. That is, the stationary phase in the open capillary column of the present invention has a very large surface area, and a long relative retention may be achieved for a sample. Increase in the retention ability may display its ability of separating complicated sample components. The open capillary column of the present invention maybe provided for high-performance separation.

When a fused silica capillary tube is used as the material of the open capillary column of the present invention, the mechanical strength is high and the structure is also stable in use.

In the open capillary column of the present invention in which oligo silica, oligo zirconia, or oligo titania is used as the base material of the stationary phase, the stationary phase having a complicated structure may be easily obtained.

The open capillary column of the present invention having a chemically-modified stationary phase of a large surface area is useful since it may be attached to a commercially available capillary electrophoresis apparatus to carry out electrochromatography. Specifically, in a commercially available capillary electrophoresis apparatus, a micro voltage may be applied to both ends of a capillary tube and, by using the micro voltage, the capillary column may be washed and conditioned and a recovery operation in the case where bubbles are generated may be performed. In electrochromatography, by sending a liquid only by an electro-endosmosis current, separation of a high height equivalent to a theoretical plate may be achieved, and an effective separation method is obtained.

What is claimed is:

1. An open capillary column comprising an open capillary tube having an inner wall with a stationary phase, a surface of which being provided with a number of pores, each of which have an expanded hollow in the stationary phase.

2. An open capillary column according to claim 1, wherein the open capillary tube is a fused silica capillary tube.

3. An open capillary column according to claim 1, wherein the open capillary tube is obtainable by cutting an open capillary tube material with an arbitrary proper length.

4. An open capillary column according to claim 1, wherein oligo silica is a base material of the stationary phase.

5. An open capillary column according to claim 4, wherein the stationary phase is a chemically modified stationary phase obtained by giving chemical modification to at least one of the surface of the stationary phase and expanded hollows in the stationary phase.

6. An open capillary column according to claim 4, wherein the surface of the stationary phase and the expanded hollows in the stationary phase are subjected to different chemical modification to obtain the chemically modified stationary phase.

7. An open capillary column according to claim 1, wherein oligo zirconia is a base material of the stationary phase.

8. An open capillary column according to claim 1, wherein oligo titania is a base material of the stationary phase.

9. An open capillary column according to claim 1, wherein the stationary phase is a chemically modified stationary phase obtained by giving chemical modification to at least one of the surface of the stationary phase and expanded hollows in the stationary phase.

10. An open capillary column according to claim 9, wherein a functional group of chemical modification is a group selected from the group consisting of alkyl group, γ-aminopropyl group, cyanoethyl group, cyclodextrin group and ion exchange group.

11. An open capillary column according to claim 1, wherein the surface of the stationary phase and the expanded hollows in the stationary phase are subjected to different chemical modifications to obtain the chemically modified stationary phase.

12. An open capillary column according to claim 11, wherein a functional group of chemical modification is a group selected from the group consisting of alkyl group, γ-aminopropyl group, cyanoethyl group, cyclodextrin group and ion exchange group.

* * * * *